United States Patent [19]

Bock et al.

[11] 4,146,559
[45] Mar. 27, 1979

[54] CYCLOALIPHATIC DIAMINES

[75] Inventors: Manfred Bock, Leverkusen; Rudolf Braden, Odenthal; Josef Pedain, Cologne, all of Fed. Rep. of Germany

[73] Assignee: Bayer Aktiengesellschaft, Leverkusen, Fed. Rep. of Germany

[21] Appl. No.: 827,767

[22] Filed: Aug. 25, 1977

[30] Foreign Application Priority Data

Aug. 27, 1976 [DE] Fed. Rep. of Germany ....... 2638731

[51] Int. Cl.² .................. C07C 87/40; C07C 87/28
[52] U.S. Cl. ................................................. 260/563 P
[58] Field of Search ..................................... 260/563 P

[56] References Cited

U.S. PATENT DOCUMENTS

| | | | |
|---|---|---|---|
| 2,635,979 | 4/1953 | Lidou | 260/563 P X |
| 3,006,954 | 10/1961 | Ramey et al. | 260/563 P X |
| 3,347,919 | 10/1967 | Martin | 260/563 P |
| 3,432,552 | 3/1969 | Kiefer et al. | 260/563 P |
| 3,449,422 | 6/1969 | Miller | 260/563 P |
| 3,456,008 | 7/1969 | Stedman | 260/563 P |
| 3,470,248 | 9/1969 | Brotherton et al. | 260/563 P |
| 3,505,402 | 4/1970 | Raff et al. | 260/563 P |
| 3,532,741 | 10/1970 | Fukunaga | 260/563 P X |
| 3,584,045 | 6/1971 | Feldman et al. | 260/563 P |
| 3,931,315 | 1/1976 | Katanosaka et al. | 260/563 P |
| 3,972,929 | 8/1976 | Kariya | 260/563 P |

Primary Examiner—Paul F. Shaver
Attorney, Agent, or Firm—Gene Harsh; Joseph C. Gil

[57] ABSTRACT

Compounds are disclosed which correspond to the general formula:

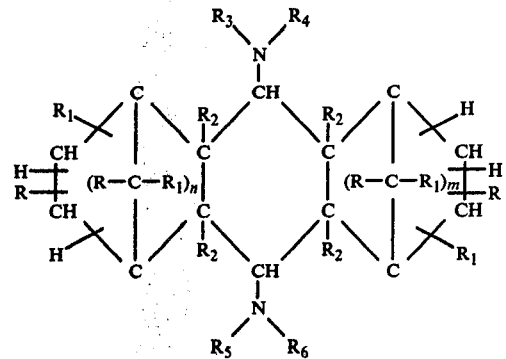

in which
n and m which are the same or different have the values 0, 1 or 2,
R, $R_1$ and $R_2$ which are the same or different, represent hydrogen or $CH_3$-groups and either
(a) $R_3$ and $R_5$ represent hydrogen and $R_4$ and $R_6$ represent hydrogen, a $C_1$-$C_{18}$ alkyl group, or a cycloalkyl group with 5 to 8 carbon atoms, or
(b) $R_3$, $R_4$, $R_5$ and $R_6$ independently represent $C_1$-$C_{18}$ alkyl groups, or cycloalkyl groups containing 5 to 8 carbon atoms, or
(c) $R_3$ and $R_4$ together and $R_5$ and $R_6$ together, in conjunction with the nitrogen atom, form a heterocyclic $C_4$-$C_6$ ring which may be interrupted by oxygen and/or nitrogen and which may be substituted by alkyl groups and/or hydroxyl alkyl groups with 1 to 4 carbon atoms.

These compounds are produced by hydrogenating the corresponding diketones in the presence of ammonia or a primary or secondary aliphatic or cycloaliphatic amine.

4 Claims, No Drawings

CYCLOALIPHATIC DIAMINES

BACKGROUND OF THE INVENTION

This invention relates to new cycloaliphatic polycyclic diamines and to their use for the production of plastics, especially light-stable and weatherproof polyurethane plastics. Aliphatic and cycloaliphatic diamines are important intermediate products which are frequently used in industry for the production of plastics. They are in particular used as chain extenders, cross-linkers or even as intermediate products for the production of isocyanates in the manufacture of light-stable polyurethane plastics. Known aliphatic and cycloaliphatic diamines include, for example, 1,6-hexamethylene diamine; 2,2,4- and 2,4,4-trimethyl hexamethylene diamine; 1,4-diaminocyclohexane; 2,4- and 2,6-diamino-1-methyl cyclohexane; 1,3-diaminomethyl cyclohexane; 3-aminomethyl-3,5,5-trimethyl cyclohexylamine; 4,4'-diaminodicyclohexyl methane; and 3,3'-dimethyl-4,4'-diaminodicyclohexyl methane. These conventional amines, however, have numerous disadvantages. For example, the lower molecular weight (cyclo)aliphatic diamines have an appreciable vapor pressure so that the atmosphere may be heavily polluted by an amine odor. Problems are also involved in handling the relatively high molecular weight solid or semicrystalline amines, such as 1,6-hexamethylene diamine, 4,4'-diaminodicyclohexyl methane or 1,4-diaminocyclohexane (cis/trans-isomer mixture) since they have to be melted before processing. In this case, the amine vapors pollute the atmosphere to a particularly serious extent.

Another disadvantage lies in the processes for synthesizing the above-mentioned diamines, some of which are extremely complex. For example, 2,4- and 2,6-diamino-1-methyl cyclohexane or 4,4'-diaminodicyclohexyl methane are obtained by the nuclear hydrogenation of corresponding aromatic intermediate products.

Accordingly, there is a need for diamines which can be produced simply and economically, are liquid at room temperature and have a low vapor pressure. A new class of cycloaliphatic diamines which have these properties and which can be produced by a simple synthesis has now surprisingly been found.

DESCRIPTION OF THE INVENTION

The present invention relates to amines corresponding to the general formula:

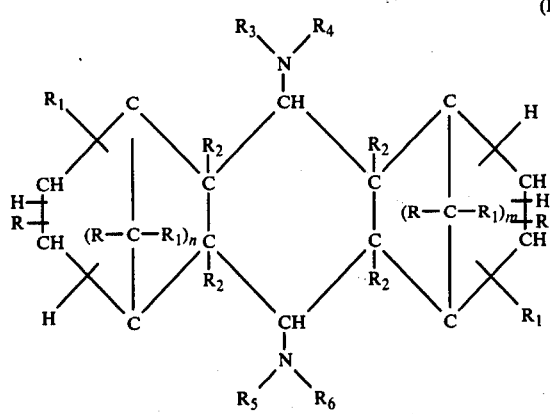

(I)

in which n and m which are the same or different have the values 0, 1 or 2,

R, $R_1$ and $R_2$ which are the same or different represent hydrogen or $CH_3$-groups, (a) $R_3$ and $R_5$ represent hydrogen and $R_4$ and $R_6$ represent hydrogen, an alkyl group with 1 to 18, preferably 1 to 4, carbon atoms which may be branched and/or may contain a hydroxyl group and/or an ether group, or a cycloalkyl group with 5 to 8 carbon atoms, (b) $R_3$, $R_4$, $R_5$ and $R_6$ independently represent alkyl groups each containing 1 to 18, preferably 1 to 4, carbon atoms which may be branched and/or may contain a hydroxyl group and/or an ether group, or cycloalkyl groups containing from 5 to 8 carbon atoms, (c) $R_3$ and $R_4$ together and $R_5$ and $R_6$ together each form with the nitrogen atom a heterocyclic ring with 4 to 6 carbon atoms which may be interrupted by oxygen and/or nitrogen and which may be substituted by alkyl groups and/or hydroxyalkyl groups with 1 to 4 carbon atoms.

The present invention also relates to a process for producing these diamines, wherein compounds corresponding to general formulae II or IIa below:

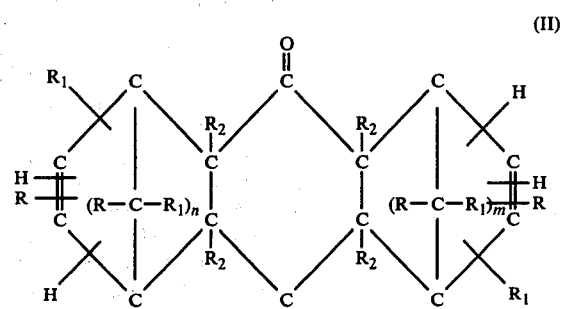

(II)

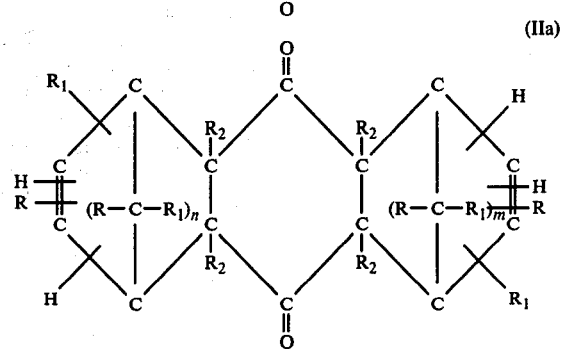

(IIa)

in which n, m, R, $R_1$ and $R_2$ are as defined above, are subjected to a hydrogenation reaction in the presence of ammonia or a primary or secondary aliphatic or cycloaliphatic amine.

Starting compounds both of the unsaturated type (II) and of the saturated type (IIa) suitable for use in the process according to the invention are known and are described, for example, in the publication by K. Alder and G. Stein in Ann., 501, 247 (1933) (hereinafter referred to as "Publication 1"). Other starting compounds of general formulae (II) and (IIa) suitable for use in the process according to the invention may be produced by methods similar to those described in Publication 1. Using such methods, unsaturated starting compounds of general formula (II) are preferably synthesized as follows:

p-Benzoquinone, or a methyl-substituted quinone, is reacted with the corresponding diene under normal pressure and at temperatures of from 20° to 150° C. in an inert solvent, preferably in toluene or methanol, at temperatures of from 50° to 100° C. The Diels-Alder product crystallizes out of the reaction solution after cooling or is obtained by distilling off the solvent, where the solvent is present in a relatively large excess. This process is particularly suitable for reactions of the above-mentioned quinones with 1,3-cyclohexadiene or cyclopentadiene or methyl derivatives thereof, both with molar reaction ratios of 1:1 and with molar reaction ratios of 1:2.

The Diels-Alder reactions of butadiene, 1-(or 2-) methyl butadiene or 2,3-dimethyl butadiene may even be carried out under autogenous pressure in the reactor in the presence of an inert solvent, such as toluene or methanol, at temperatures of from 50° to 180° C., preferably at temperatures of from 120° to 170° C.

Depending upon the quantity of solvent used, the reaction product is obtained in either crystalline form or in the form of a solution from which it may be isolated by distilling off the solvent.

For producing mixed Diels-Alder products, 1 mol of diene is initially added with the quinone by the two above-described processes (in the absence of pressure or under autogenous pressure), followed by the addition of another mol of another diene, either after isolation of the mono-adduct or, better still, even without intermediate working up of this stage.

Saturated starting compounds of general formula (IIa) are, for example, obtained by hydrogenating compounds of general formula (II) in alcoholic solution with hydrogen in the presence of colloidal palladium.

As mentioned above, the quinones used for producing the starting substances (II) are p-benzoquinone and methyl-substituted quinones, preferably 2-methyl benzoquinone, 2,3-dimethyl benzoquinone, 2,5-dimethyl benzoquinone and 2,6-dimethyl benzoquinone. The following compounds are examples of dienes: cyclopentadiene, methyl and dimethyl cyclopentadiene (cf. the publication by R. Riemschneider and E. B. Grabitz in Monatshefte 89, pages 748–53 (1958); hereinafter referred to as "Publication 2"), 1,3-cyclohexadiene, 1-methyl butadiene, 2-methyl butadiene and 2,3-dimethyl butadiene.

The intermediate products (II) and (IIa), synthesized from these dienes and the above-mentioned quinones, are present in a complex mixture of various possible stereoisomers (cf. Hill R., Martin J., Stauch W., J. Am. Chem. Soc., 83, (1961); de Vries L., Heck R., Piccolini R., Winstein S., Chem. a. Ind., 45 1416 (1959).

The following are examples of compounds corresponding to general formula (II):

(a) the 1:2-adducts of p-benzoquinone or 1-methyl benzoquinone, 2,3-, 2,5- or 2,6-dimethyl benzoquinone and cyclopentadiene, methyl cyclopentadiene (Publication 2), dimethyl cyclopentadiene (Publication 2), 1,3-cyclohexadiene, 1-methyl butadiene, 2-methyl butadiene and 2,3-dimethyl butadiene;

(b) the reaction products of the 1:1 Diels-Alder adducts of cyclopentadiene and p-benzoquinone or 1-methyl benzoquinone; 2,3-, 2,5- or 2,6-dimethyl benzoquinone with methyl cyclopentadiene (Publication 2), dimethyl cyclopentadiene (Publication 2), 1,3-cyclohexadiene, butadiene, 1-methyl butadiene, 2-methyl butadiene and 2,3-dimethyl butadiene;

(c) the reaction products of the 1:1 Diels-Alder adducts of methyl cyclopentadiene and p-benzoquinone or 1-methyl benzoquinone; 2,3-, 2,5- or 2,6-dimethyl benzoquinone which dimethyl cyclopentadiene (Publication 2), 1,3-cyclohexadiene, butadiene, 1-methyl butadiene, 2-methyl butadiene and 2,3-dimethyl butadiene;

(d) the reaction products of the 1:1 Diels-Alder adducts of dimethyl cyclopentadiene and p-benzoquinone or 1-methyl benzoquinone; 2,3-,2,5- or 2,6-dimethyl benzoquinone with 1,3-cyclohexadiene, butadiene, 1-methyl butadiene, 2-methyl butadiene and 2,3-dimethyl butadiene;

(e) the reaction products of the 1:1 Diels-Alder adducts of 1,3-cyclohexadiene and p-benzoquinone or 1-methyl benzoquinone; 2,3-, 2,5- or 2,6-dimethyl benzoquinone with butadiene, 1-methyl butadiene, 2-methyl butadiene and 2,3-dimethyl butadiene;

(f) the reaction products of the 1:1 Diels-Alder adducts of butadiene and p-benzoquinone or 1-methyl benzoquinone; 2,3- 2,5- or 2,6-dimethyl benzoquinone with 1-methyl butadiene, 2-methyl butadiene and 2,3-dimethyl butadiene;

(g) the reaction products of the 1:1 Diels-Alder adducts of 2-methyl butadiene and p-benzoquinone or 1-methyl benzoquinone; 2,3-, 2,5- or 2,6-dimethyl benzoquinone with 2,3-dimethyl butadiene.

Accordingly, examples of the starting products for the amines according to the invention are compounds with the following structural formulae:

1,4:5,8-dimethano-1,4,4a,5a,5,8,8a, 9a-octahydroanthraquinone (III)

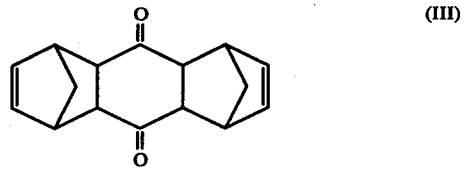

1,4-methano-1,4,4a,5a, 5, 8, 8a, 9a-octahydroanthraquinone (IV)

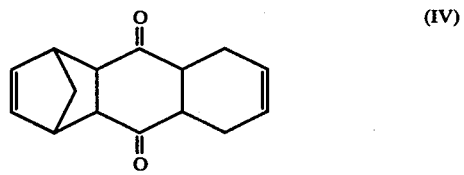

2-methyl-5,8-methano-1,4,4a, 5a, 5, 8, 8a, 9a-octahydroanthraquinone (V)

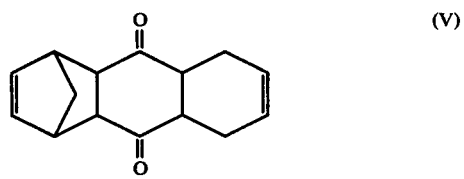

1,4,4a,5a,5,8,8a,9a-octahydroanthraquinone (VI)

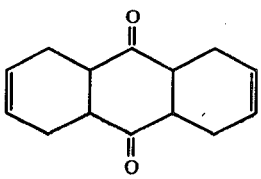

2-methyl-1,4,4a,5a,5,8,8a,9a-octahydroanthraquinone (VII)

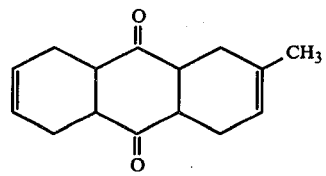

the stereoisomers 2,6- (or 2,7-) dimethyl-1,4,4a,5a,5,8-,8a,9a-octahydroanthraquinone (VIII)

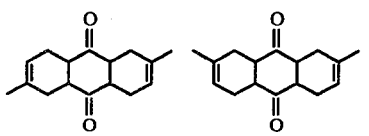

and also the corresponding saturated diketones.

To produce the diamines according to the invention, the intermediate products (II) and (IIa) described above are catalytically hydrogenated in known manner in the presence of ammonia, primary or secondary amines.

Suitable amines include, for example, methyl, ethyl, isopropyl, propyl, isobutyl, n-butyl, sec.-butyl, tert.-butyl, tert.-pentyl, hexyl, 2-ethyl hexyl, dodecyl, cetyl, stearyl, 2-hydroxyethyl, 2-methoxyethyl, 3-hydroxy propyl, 3-ethoxy propyl, 2-hydroxy propyl, 3-hydroxy butyl, cyclohexyl, cyclohexyl methyl, 3-methyl cyclohexyl, 4-methyl cyclohexyl, 3,3,5-trimethyl cyclohexyl and 4-methyl cyclohexyl methyl amine. Also suitable are tetrahydrofurfurylamine, pyrrolidine, piperidine, morpholino, hexamethylene imine, N-methyl piperazine, N-2-hydroxyethyl piperazine, dimethyl, diethyl and dibutylamine, as well as N-methyl octadecyl, N-methyl cyclohexyl, N-ethyl cyclohexyl and bis-(2-hydroxyethyl)amine.

Hydrogenation of the compounds of general formula (II) is accompanied by the reductive amination of the CO-groups and by the addition of hydrogen to the C=C-double bonds. Reduction is generally carried out in the presence of 2 to 30 mols of ammonia or amine per mol of compound (II), preferably in the presence of 3 to 15 mols of ammonia or amine per mol of compound (II), at a temperature of about 30° to 180° C. under a hydrogen pressure of 5 to 200 bars, preferably at 60° to 150° C. under a hydrogen pressure of 30 to 150 bars.

The usual hydrogenation catalysts may be used in the process of the invention. Suitable hydrogenation catalysts are, for example, those which contain one element or several elements of Group VIII of the Periodic System in metallic or oxidic form. The catalytically active component may be used without a substrate or may be applied to a substrate. Substrates for the active constituents include such compounds as alumina, carbon, kieselguhr, bentonite, asbestos, silica or zinc oxide. Suitable catalysts include, for example, nickel, cobalt, rhodium, ruthenium and platinum catalysts and also, for example, Raney nickel, Raney cobalt, nickel or kieselguhr with a nickel content of up to 60% by weight, cobalt oxide on kieselguhr, nickel chromite or platinum on carbon with a Pt-content of from 0.1 to 5% by weight. In many cases, it is of advantage to use catalytic quantities of acids such as phosphoric acid, hydrochloric acid, formic acid, acetic acid, and their ammonium salts, including ammonium carbonate.

Hydrogenation may be carried out either in the presence or in the absence of a solvent. Suitable solvents for hydrogenation in solution include, for example, alcohols; ethers; cyclic ethers, such as tetrahydrofuran and dioxane; and hydrocarbons such as cyclohexane, benzene, toluene and xylene. In some cases, it can also be of advantage to use a mixture of solvents. A particular advantage of the process according to the invention is that the reductive amination reaction can be carried out in the same solvent in which the Diels-Alder adduct was produced.

In the production of the saturated Diels-Alder compound of general formula (IIa), hydrogenation according to Publication 1 is carried out in an inert solvent, such as ethyl alcohol, with colloidal palladium, for example, at room temperature in a hydrogen atmosphere. The C=C—double bonds are hydrogenated with the two keto groups remaining intact. Thereafter, the saturated diketones (IIa) are subjected to reductive amination as described. In a particular variation of the process according to the invention, the two hydrogenation reactions may be carried out successively by a one-pot process. The C=C—double bonds of the starting compounds (II) are initially hydrogenated in the manner indicated, after which the keto groups are subjected to reductive amination in accordance with the invention in the same solvent without intermediate working up of stage (IIa).

In another particular embodiment of the invention, the diketone compounds (II) and (IIa) are initially reacted with secondary amines under dehydrating conditions, for example in boiling benzene, toluene or xylene, in known manner to form Schiff's bases. The Schiff's bases thus obtained are then hydrogenated in accordance with the invention.

Particularly preferred representatives of the products (I) according to the invention are the amines obtainable from the Diels-Alder adducts (III)–(VIII) mentioned by way of example above and their configuration isomers, such as:

9,10-diamino-1,4:5,8-dimethano-tetradecahydroanthracene (IX)

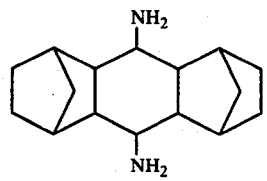

9,10-diamino-1,4-methano-tetradecahydroanthracene (X)

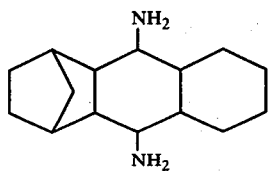

9,10-diamino-1,4-methano-6-methyl-tetradecahydroanthracene (XI)

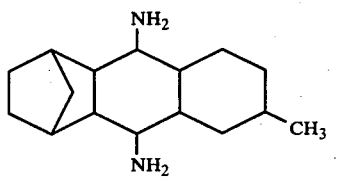

9,10-diaminotetradecahydroanthracene (XII)

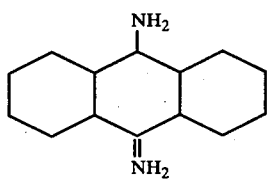

9,10-diamino-2-methyl-tetradecahydroanthracene (XIII)

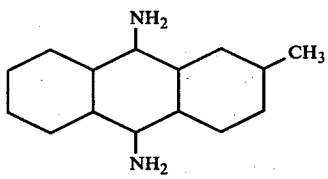

9,10-diamino-2,6 (or 2,7)-dimethyl-tetradecahydroanthracene (XIV)

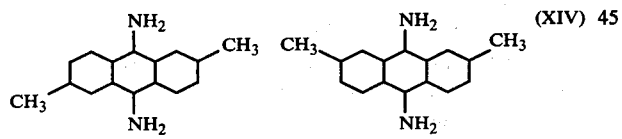

The following diamines are also representative examples of products of the invention: N,N'-dimethyl-9,10-diamino-2,6 (or 2,7)-dimethyl-tetradecahydroanthracene (XV)

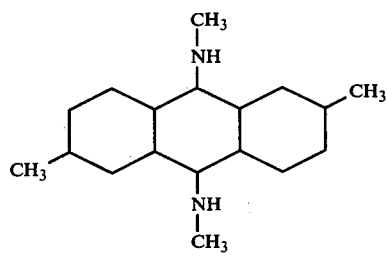

N,N'-diisopropyl-9,10-diamino-1,4:5,8-dimethano-tetradecahydroanthracene (XVI)

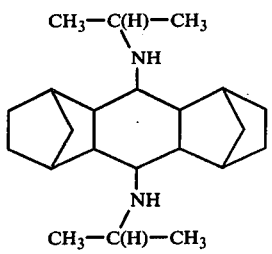

N,N'-distearyl-9,10-diamino-1,4:5,8-dimethano-tetradecahydroanthracene (XVII)

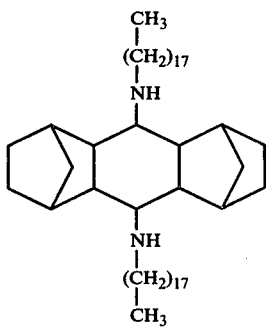

N,N'-dimorpholino-9,10-diamino-1,4:5,8-dimethano-tetradecahydroanthracene (XVIII)

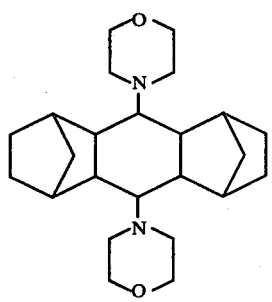

The diamines according to the invention are generally clear viscous liquids at 20° C. They have a low vapor pressure and virtually no odor of their own. Accordingly, they are also physiologically safe to handle.

The primary and secondary amines according to the invention are particularly suitable for the production of polyurethane ureas. By reaction with isocyanate prepolymers based on aliphatic and cycloaliphatic diisocyanates, it is possible for example to obtain high quality light-stable coating compositions by methods known per se as described in U.S. Pat. Nos. 3,936,409 and 3,734,894; German Offenlegungsschrift No. 1,694,277 and U.S. Pat. No. 3,752,786. With isocyanate prepolymers based on aromatic diisocyanates, it is for example possible to produce cast elastomers with high flexibility.

The diamines of the invention are also particularly suitable for use as crosslinkers for masked isocyanates. They may also be successfully used as hardeners for epoxide resins. The diisocyanates obtained by phosgenation from the diamines claimed in accordance with the invention may in turn be further processed into light stable polyurethanes or polyurethanes ureas with outstanding mechanical properties.

However, the diamines according to the invention are preferably used as chain extenders and crosslinkers in the production of polyurethane ureas. Accordingly, the present invention also relates to a process for the production of optionally cellular polyurethane ureas by reacting (a) polyisocyanates and/or NCO-prepolymers of polyisocyanates and relatively high molecular weight and/or low molecular weight compounds containing isocyanate-reactive groups, with
(b) cycloaliphatic primary or secondary diamines, optionally in the presence of
(c) blowing agents, catalysts and other additives known per se, wherein the diamines according to the invention are used as component (b).

Starting components suitable for the production of polyurethane plastics include aliphatic, cycloaliphatic, araliphatic, aromatic and heterocyclic polyisocyanates of the type described for example, by W. Siefken in Justus Liebigs Annalen der Chemie, 526, pages 75 to 136, for example ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate; also any mixtures of these isomers; 1-isocyanato-3,3,5-trimethyl-5-isocyanatomethyl cyclohexane as described in German Auslegeschrift No. 1,202,785 and U.S. Pat. No. 3,401,190; 2,4- and 2,6-hexahydrotolylene diisocyanate and any mixtures of these isomers; hexahydro-1,3- and/or 1,4-phenylene diisocyanate; perhydro-2,4'- and/or -4,4'-diphenyl methane diisocyanate; 1,3- and 1,4-phenylene diisocyanate; 2,4- and 2,6-tolylene diisocyanate and any mixtures of these isomers; diphenyl methane-2,4'- and/or -4,4'-diisocyanate; naphthylene-1,5-diisocyanate; triphenyl methane-4,4', 4''-triisocyanate; polyphenyl polymethylene polyisocyanates, of the type which can be obtained by condensing aniline with formaldehyde, followed by phosgenation, and which are described, for example, in British Pat. Nos. 874,430 and 848,671; m- and p-isocyanatophenyl sulphonyl isocyanates according to U.S. Pat. No. 3,454,606; perchlorinated aryl polyisocyanates of the type described, for example, in German Auslegeschrift No. 1,157,601 (U.S. Pat. No. 3,277,138); polyisocyanates containing carbodiimide groups of the type described in German Pat. No. 1,092,007 (U.S. Pat. No. 3,152,162); diisocyanates of the type described in U.S. Pat. No. 3,492,330; polyisocyanates containing allophanate groups of the type described, for example, in British Pat. No. 994,890; Belgian Pat. No. 761,626 and published Dutch Patent Application No. 7,102,524; polyisocyanates containing isocyanurate groups of the type described, for example, in U.S. Pat. No. 3,001,973; German Pat. Nos. 1,022,789; 1,222,067 and 1,027,394 and in German Offenlegungsschriften Nos. 1,929,034 and 2,004,048; polyisocyanates containing urethane groups of the type described, for example, in Belgian Pat. No. 752,261 or U.S. Pat. No. 3,394,164; polyisocyanates containing acylated urea groups according to German Pat. No. 1,230,778; polyisocyanates containing biuret groups of the type described, for example, in German Pat. No. 1,101,394 (U.S. Pat. Nos. 3,124,605 and 3,201,372) and in British Pat. No. 889,050; polyisocyanates obtained by telomerization reactions of the type described, for example, in U.S. Pat. No. 3,654,106; polyisocyanates containing ester groups of the type described, for example, in British Pat. Nos. 965,474 and 1,072,965; U.S. Pat. No. 3,567,763 and in German Pat. No. 1,231,688, and reaction products of the above-mentioned isocyanates with acetals according to German Pat. No. 1,072,385 and polyisocyanates containing polymeric fatty acid radicals according to U.S. Pat. No. 3,455,883.

It is also possible to use the isocyanate-group-containing distillation residues accumulating in the production of isocyanates on a commercial scale, if desired in solution in one or more of the aforementioned polyisocyanates. It is also possible to use any mixtures of the aforementioned polyisocyanates.

In general, it is particularly preferred to use the readily available polyisocyanates, for example, 2,4- and 2,6-tolylene diisocyanate, and any mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates").

As explained above, aliphatic and cycloaliphatic diisocyanates, in particular 1,6-hexane diisocyanate, 4,4'-dicyclohexyl methane diisocyanate and 1-isocyanato-3-isocyanatomethyl-3,5,5-trimethyl cyclohexane, are particularly preferred for the production of light-stable coatings.

Starting components which may be used for the production of isocyanate prepolymers are compounds containing at least two isocyanate-reactive hydrogen atoms and having a molecular weight generally in the range from 400 to 10,000. In addition to compounds containing amino groups, thiol groups or carboxyl groups, compounds of this type are preferably polyhydroxyl compounds, more especially compounds containing from two to eight hydroxyl groups, particularly those with molecular weights in the range from 800 to 10,000, preferably in the range from 1000 to 6000. These include polyesters, polyethers, polythioethers, polyacetals, polycarbonates and polyester amides containing at least 2, generally 2 to 8, but preferably 2 to 4 hydroxyl groups, of the type commonly used for the production of homogeneous and cellular polyurethanes.

Examples of suitable polyesters containing hydroxyl groups are reaction products of polyhydric, preferably dihydric and, optionally, trihydric alcohols and polybasic, preferably dibasic carboxylic acids. Instead of the free polycarboxylic acids, the corresponding polycarboxylic acid anhydrides or corresponding polycarboxylic acid esters of lower alcohols or mixtures thereof may also be used for the production of the polyesters. The polycarboxylic acids may be aliphatic, cycloaliphatic, aromatic and/or heterocyclic, and may optionally be substituted, for example by halogen atoms, and/or unsaturated.

Examples of these polycarboxylic acids are succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, which may be mixed with monomeric fatty acids, terephthalic acid dimethyl ester, terephthalic acid-bis-glycol ester. Examples of suitable polyhydric alcohols are ethylene glycol, 1,2- and 1,3-propylene glycol, 1,4- and 2,3-butylene glycol, 1,6-hexanediol, 1,8-octanediol, neopentyl glycol, cyclohexane dimethanol (1,4-bis-hydroxy methyl cyclohexane), 2-methyl-1,3-propane diol, glycerol, trimethylol propane, 1,2,6-hexane triol, 1,2,4-butane triol, trimethylol ethane, pentaerythritol, quinitol, mannitol and sorbitol, methyl glycoside, also diethylene glycol, triethylene glycol, tetraethylene glycol, polyethylene glycols, dipropylene glycol, polypropylene glycols, dibutylene glycol and polybutylene glycols. The polyesters may contain terminal carboxyl groups. Polyesters of lactones, for example ε-caprolactone or hydroxy carboxylic acids, for example ω-hydroxy caproic acid, may also be used.

The polyethers containing at least 2, generally 2 to 8 and preferably 2 to 3 hydroxyl groups which are used in accordance with the invention are also known per se and are obtained, for example, by polymerizing epoxides such as ethylene oxide, propylene oxide, butylene oxide, tetrahydrofuran, styrene oxide or epichlorhydrin on their own, for example in the presence of boron trifluoride, or by adding these epoxides, either as mixtures or successively, with starter components containing reactive hydrogen atoms, such as alcohols or amines, for example water, ethylene glycol, 1,3- or 1,2-propylene glycol, trimethylol propane, 4,4'-dihydroxy diphenyl propane, aniline, ammonia, ethanolamine, ethylene diamine. Sucrose polyethers of the type described, for example, in German Auslegeschriften Nos. 1,176,358 and 1,064,938, may also be used in accordance with the invention. In many cases, it is preferred to use polyethers which contain predominantly primary hydroxyl groups up to 90% by weight, based on all the hydroxyl groups present in the polyether. Polyethers modified by vinyl polymers, of the type formed for example by polymerizing styrene and acrylonitrile in the presence of polyethers as described in U.S. Pat. Nos. 3,383,351; 3,304,273; 3,523,093; and 3,110,695 and German Pat. No. 1,152,536 are also suitable, as are polybutadienes containing hydroxyl groups.

Among the polythioethers, reference is made in particular to the condensation products of thiodiglycol with itself and/or with other glycols, dicarboxylic acids, formaldehyde, amino carboxylic acids or amino alcohols. Depending upon the co-components, these products are polythio mixed ethers, polythioether esters, polythioether ester amides.

Suitable polyacetals are, for example, those compounds which can be obtained from glycols, such as diethylene glycol, triethylene glycol, 4,4'-dioxethoxy diphenyl dimethyl methane, hexane diol and formaldehyde. Polyacetals suitable for the purposes of the invention may also be obtained by polymerizing cyclic acetals.

Suitable polycarbonates containing hydroxyl groups are those known per se which can be obtained, for example, by reacting diols such as 1,3-propane diol, 1,4-butane diol and/or 1,6-hexane diol, diethylene glycol, triethylene glycol, tetraethylene glycol, with diaryl carbonates, for example diphenyl carbonate or phosgene.

Examples of the polyester amides and polyamides are the predominantly linear condensates obtained from polybasic, saturated and unsaturated carboxylic acids and their anhydrides and polyhydric saturated and unsaturated amino alcohols, diamines, polyamines and their mixtures.

Polyhydroxyl compounds already containing urethane or urea groups and optionally modified natural polyols such as castor oil, carbohydrates, starch, may also be used. Addition products of alkylene oxides with phenol-formaldehyde resins or even with urea-formaldehyde resins may also be used.

Representatives of these compounds used in accordance with the invention are described, for example, in High Polymers, Vol. XVI, "Polyurethanes, Chemistry and Technology", by Saunders-Frisch, Interscience Publishers, New York, London, Vol. I, 1962, pages 32 to 42 and pages 44 to 54, and Vol. II, 1964, pages 5–6 and 198–199, and in Kunststoff-Handbuch, Vol. III, Vieweg-Hochtlen, Carl Hanser-Verlag, Munich, 1966, for example on pages 45 to 71.

It is of course possible to use mixtures of the abovementioned compounds containing at least two isocyanate-reactive hydrogen atoms and having molecular weights of from 400 to 10,000, for example mixtures of polyethers and polyesters.

Other starting components which may be used for the production of isocyanate prepolymers are compounds containing at least two isocyanate-reactive hydrogen atoms and having a molecular weight in the range from 32 to 400. In this case, too, the compounds in question are compounds containing hydroxyl groups and/or amino groups and/or thiol groups and/or carboxyl groups, preferably compounds containing hydroxyl groups and/or amino groups which are used as chain extenders or crosslinkers. These compounds generally contain from 2 to 8 isocyanate-reactive hydrogen atoms, preferably 2 or 3 reactive hydrogen atoms.

Examples of compounds such as these are ethylene glycol, 1,2-propylene glycol and 1,3-propylene glycol, 1,4-butylene glycol and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, trimethylol ethane, pentaerythritol, quinitol, mannitol and sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxy diphenyl propane, dihydroxy methyl hydroquinone, ethanolamine, diethanolamine, triethanolamine, 3-aminopropanol, ethylene diamine, 1,3-diaminopropane, 1-mercapto-3-aminopropane, 4-hydroxy- or -aminophthalic acid, succinic acid, adipic acid, hydrazine, N,N'-dimethyl hydrazine, 4,4'-diaminodiphenyl methane, tolylene diamine, methylene-bis-chloraniline, methylene-bis-anthranilic acid ester, diaminobenzoic acid esters and the isomeric chlorophenylene diamines.

In this case, too, it is possible to use mixtures of different compounds containing at least two isocyanate-reactive hydrogen atoms and having a molecular weight in the range of from 32 to 400.

However, it is also possible in accordance with the invention to use polyhydroxyl compounds containing high molecular weight polyadducts or polycondensates in finely disperse or dissolved form. Modified polyhydroxyl compounds such as these are obtained by carrying out polyaddition reactions (for example reactions between polyisocyanates and aminofunctional compounds) or polycondensation reactions (for example between formaldehyde and phenols and/or amines) directly in situ in the above-mentioned compounds containing hydroxyl groups. Processes such as these are described, for example, in German Auslegeschriften Nos. 1,168,075 and 1,260,142 and in German Offenlegungsschriften Nos. 2,324,134; 2,423,984; 2,512,385;

2,513,815; 2,550,796; 2,550,797; 2,550,833 and 2,550,862. However, it is also possible, in accorrdance with U.S. Pat. No. 3,869,413 or German Offenlegungsschrift No. 2,550,860, to mix an aqueous polymer dispersion with a polyhydroxyl compound and subsequently to remove the water from the mixture.

In cases where modified polyhydroxyl compounds of the type mentioned above are used as starting components in the polyisocyanate polyaddition process, polyurethane plastics with considerably improved mechanical properties are often formed.

In cases where it is desired to produce cellular polyurethane ureas, water and/or readily volatile organic substances may be used as blowing agents in the production of foamed polyurethane plastics. Suitable organic blowing agents include acetone; ethyl acetate; halogen-substitued alkanes such as methylene chloride, chloroform, ethylidene chloride, vinylidene chloride, monofluorotrichloromethane, chlorodifluoromethane, dichlorodifluoromethane; and butane, hexane, heptane or diethyl ester. A blowing effect can also be obtained by adding compounds which decompose at temperatures above room temperature giving off gases, for example nitrogen, and azocompounds such as azoisobutyronitrile. Other examples of blowing agents and information on the use of blowing agents may be found in Kunststoff-Handbuch, Vol. VII, by Vieweg and Hochtlen, Carl-Hanser-Verlag, Munich 1966, for example on pages 108 and 109, 453 to 455 and 507 to 510.

According to the invention, catalysts are also frequently used. Examples of suitable catalysts are those known per se, for example tertiary amines such as triethyl amine, tributyl amine, N-methyl morpholine, N-ethyl morpholine, N-cocomorpholine, N,N,N',N'-tetramethyl ethylene diamine, 1,4-diazabicyclo-(2,2,2)-octane, N-methyl-N'-dimethyl aminoethyl piperazine, N,N-dimethyl benzyl amine, bis-(N,N-diethyl amino ethyl)-adipate, N,N-diethyl benzyl amine, pentamethyl diethylene triamine, N,N-dimethyl cyclohexyl amine, N,N,N',N'-tetramethyl-1,3-butane diamine, N,N-dimethyl-β-phenyl ethyl amine, 1,2-dimethyl imidazole, 2-methyl imidazole. Other suitable catalysts are Mannich bases known per se of secondary amines, such as dimethyl amine, and aldehydes, preferably formaldehyde, or ketones such as acetone, methyl ethyl ketone or cyclohexanone, and phenols such as phenol, nonylphenol or bisphenol.

Examples of tertiary amine catalysts containing isocyanate-reactive hydrogen atoms are triethanolamine, triisopropanol-amine, N-methyl diethanolamine, N-ethyl diethanolamine, N,N-dimethyl ethanolamine, also their reaction products with alkylene oxides, such as propylene oxide and/or ethylene oxide.

Other suitable catalysts are sila-amines with carbon-silicon bonds of the type described, for example, in German Patent No. 1,229,290 (corresponding to U.S. Pat. No. 3,620,984), for example 2,2,4-trimethyl-2-silamorpholine and 1,3-diethyl aminoethyl tetramethyl disiloxane.

Other suitable catalysts are nitrogen-containing bases, such as teraalkyl ammonium hydroxides; alkali metal hydroxides such as sodium hydroxide; alkali metal phenolates such as sodium phenolate or alkali metal alcoholates such as sodium methylate. Hexahydrotriazines may also be used as catalysts.

According to the invention, organometallic compounds, especially organo tin compounds, may also be used as catalysts.

Preferred organo tin compounds are tin(II)salts of carboxylic acids such as tin(II)acetate, tin(II)octoate, tin(II)ethyl hexoate and tin(II)laurate, and the tin(IV)-compounds, for example dibutyl tin oxide, dibutyl tin dichloride, dibutyl tin diacetate, dibutyl tin dilaurate, dibutyl tin maleate or dioctyl tin diacetate. It is of course possible to use all of the above-mentioned catalysts in the form of mixtures.

Further representatives of catalysts suitable for use in accordance with the invention and details on the way in which the catalysts work may be found in Kungststoff-Handbuch, Vol. VII, by Vieweg and Hochtlen, Carl-Hanser Verlag, Munich, 1966, for example on pages 96 to 102.

The catalysts are generally used in quantities of from about 0.001 to 10% by weight, based on the quantity of compounds with at least two isocyanate-reactive hydrogen atoms and a molecular weight in the range from 400 to 10,000.

According to the invention, surface-active additives, such as emulsifiers and foam stabilizers, may also be used. Examples of emulsifiers are the sodium salts of castor oil sulphonates or salts of fatty acids with amines such as diethyl amine/oleic acid or diethanolamine/stearic acid. Alkali or ammonium salts of sulphonic acids, such as those of dodecyl benzene sulphonic acid or dinaphthyl methane disulphonic acid or of fatty acids, such as ricin-oleic acid, or of polymeric fatty acids, may also be used as surface-active additives.

Particularly suitable foam stabilizers are the polyether siloxanes, especially those which are water-soluble. These compounds generally have a structure in which a copolymer of ethylene oxide and propylene oxide is attached to a polydimethyl siloxane radical. Foam stabilizers of this kind are described, for example, in U.S. Pat. Nos. 2,834,748; 2,917,480 and 3,629,308.

According to the invention, it is also possible to use reaction retarders, for example substances with an acid reaction such as hydrochloric acid or organic acid halides; cell regulators known per se, such as paraffins or fatty alcohols or dimethyl polysiloxanes; pigments or dyes and flameproofing agents known per se, for example trischlorethyl phosphate, tricresyl phosphate or ammonium phosphate and polyphosphate; stabilizers against the effects of ageing and weather; plasticizers and substances with fungistatic and bacteriostatic effects; and fillers such as barium sulphate, kieselguhr, carbon black or prepared chalk.

Other examples of the surface-active additives and foam stabilizers which may be used in accordance with the invention and of cell regulators, reaction retarders, stabilizers, flameproofing substances, plasticizers, dyes and fillers, substances with fungistatic and bacteriostatic effects, and also details on the way in which these additives are to be used and how they work, can be found in Kunststoff-Handbuch, Vol. VII, published by Vieweg and Hochtlen, Carl-Hanser-Verlag, Munich, 1966, for example on pages 103 to 113.

The diamines according to the invention containing secondary or tertiary amino groups are suitable for use as corrosion inhibitors and as catalysts for polyisocyanate polyaddition reactions.

So far as the starting components for the polyisocyanate polyaddition process are concerned, reference is made to the above-mentioned compounds. The invention also relates to the use of the tertiary amines according to the invention as catalyst for isocyanate reactions.

The invention is illustrated by the following Examples.

EXAMPLES

EXAMPLE 1

9,10-Diamino-1,4:5,8-dimethano-tetradecahydroanthracene (IX)

This Example shows that both compounds of general formula (II) (method A) and also compounds of type (IIa) (method B) may be used in accordance with the invention as starting products for the synthesis of amines.

Method A 300 g of 1,4:5,8-dimethano-1,4,4a,5a,5,8,8a, 9a-octahydroanthraquinone (1.25 mols) are hydrogenated for 4 hours at 140° to 150° C. under a hydrogen pressure of 120 to 150 bars in 1000 ml of methanol in the presence of 15 g of Raney cobalt catalyst, 360 g of liquid ammonia and 7 g of glacial acetic acid. The catalyst is then separated off and the reaction product is distilled following the removal of excess solvent. The diamine (IX) boils at 157 to 159° C./0.1 Torr and is obtained as a colorless viscous liquid in a yield of 280 g (91% of the theoretical).

$n_D^{25}$:1.5613. Analysis: (here and in the following always % by weight). Observed: C 78.2; H 10.78; N 11.42. Theoretical: C 78.1; H 10.57; N 11.38.

Method B 200 g of 1,4:5,8-dimethano-perhydroanthraquinone (0.98 mol) are hydrogenated for 3 hours at 140° to 150° C. under a hydrogen pressure of 120 to 150 bars in 1000 ml of methanol in the presence of 10 g of Raney cobalt catalyst, 360 g of liquid ammonia and 7 g of glacial acetic acid. The catalyst is then separated off and the reaction product is distilled off in a high vacuum following removal of the solvent. 9,10-Diamino-1,4:5,8-dimethano-tetradecahydroanthracene (IX) is isolated in a yield of 192 g (95%), its analytical and spectroscopic data being completely identical with those of the diamine obtained in Example 1A.

EXAMPLE 2

9,10-Diamino-tetradecahydroanthracene (XII)

200 g of 1,4,4a,5a,5,8,8a,9a-octahydroanthraquinone (0.025 mol), dissolved in 1000 ml of dioxane, are hydrogenated for 3 hours at 150° C. under a hydrogen pressure of 120 to 150 bars in the presence of 10 g of Raney cobalt catalyst, 200 g of liquid ammonia and 5 g of glacial acetic acid. The catalyst is then distilled off and the reaction mixture is distilled. The diamine (XII) boils at 130° C./0.015 Torr and is obtained in a yield of 165 g (80%).

$n_D^{25}$:1.5362. Analysis: Observed: C 75.50; H 11.82; N 12.72; Theoretical: C 75.67; H 11.71; N 12.61.

EXAMPLE 3

9,10-Diamino-2,6 (or 2,7)-dimethyl tetradecahydroanthracene (XIV)

300 g of 2,6 (or 2,7)-dimethyl-1,4,4a,5a,5,8,8a,9a-octahydroanthraquinone (1.23 mols) are dissolved in 1200 ml of dioxane and hydrogenated for 3 hours at 150° C. under a hydrogen pressure of 120 to 150 bars in the presence of 360 g of liquid ammonia, 7 g of glacial acetic acid and 15 g of Raney cobalt catalyst. After the catalyst has been separated off, the reaction mixture is worked up by distillation. The diamine (XIV) boils at 141° to 144° C./0.08 Torr and is obtained in a yield of 292 g (95%).

$n_D^{25}$:1.5514. Analysis: Observed: C 76.2; H 12.11; N 11.15; Theoretical: C 76.8; H 12.0; N 11.20.

EXAMPLE 4

9,10-Diamino-1,4-methano-tetradecahydroanthracene (X)

250 g of 1,4-methano-1,4,4a,5a,5,8,8a,9a-octahydroanthraquinone (1.1 mol), dissolved in 1000 ml of methanol, are hydrogenated for 3 hours at 150° C. under a hydrogen pressure of 120 to 150 bars in the presence of 300 g of liquid ammonia, 8 g of glacial acetic acid and 12 g of Raney cobalt catalyst. After the catalyst has been separated off and the solvent distilled off, the reaction mixture is worked up by distillation in a high vacuum. The amine (X) boils at 137° to 139° C./0.08 Torr and is obtained in a yield of 200 g (78%).

$n_D^{25}$:1.5556. Analysis: Observed: C 76.40; H 12.0; N 12.05; Theoretical: C 76.92; H 11.11; N 11.96.

EXAMPLE 5

9,10-Diamino-1,4-methano-6-methyl-tetradecahydroanthracene (XI)

300 g of 6-methyl-1,4-methano-1,4,4a,5a,5,8,8a,9a-octahydroanthraquinone (1.24 mols) give 274 g (89%) of diamine when hydrogenated in 1000 ml of methanol in the presence of 480 g of liquid ammonia, 8 g of glacial acetic acid and 15 g of Raney cobalt catalyst. Hydrogenation is carried out over a period of 3 hours at 150° C. at a hydrogen pressure of 120 to 150 bars. The diamine is obtained from the crude product by distillation in a high vacuum at 137° C./0.1 Torr.

$n_D^{25}$:1.5584. Analysis: Observed: C 77.0; H 12.10; N 11.34; Theoretical: C 77.42; H 11.29; N 11.29.

EXAMPLE 6

9,10-Diamino-2-methyl-tetradecahydroanthracene (XIII)

300 g of 2-methyl-1,4,4a,5a,5,8,8a,9a-octahydroanthraquinone (1.3 mols) are hydrogenated as in Example 5 for 3 hours at 150° C. under a hydrogen pressure of 120 to 150 bars in 1000 ml of methanol in the presence of 480 g of liquid ammonia, 8 g of glacial acetic acid and 15 g of Raney cobalt catalyst. After separation of the catalysts, the diamine is obtained from the crude product by distillation in a high vacuum at 135° C./0.12 Torr.

Yield: 256 g (83%). $n_D^{25}$:1.5473. Analysis: Observed: C 76.15; H 12.03; N 12.11; Theoretical: C 76.27; H 11.86; N 11.86.

EXAMPLE 7

N,N'-Dimethyl-9,10-diamino-2,6 (or 2,7)-dimethyl-tetradecahydroanthracene (XV)

300 g of 2,6 (or 2,7)-dimethyl-1,4,4a,5a,5,8,8a,9a-octahydroanthraquinone (1.23 mols) are hydrogenated for 4 hours at 120° to 150° C. under a hydrogen pressure of 120 to 150 bars in 1200 ml of methanol in the presence of 300 g of methylamine and 15 g of Raney cobalt catalyst. After the catalyst has been separated off, the reaction mixture is worked up by distillation, the diamine (XV) being obtained in the form of a yellowish viscous liquid at 158° C./0.2 Torr.

Yield: 290 g (85% of the theoretical). $n_D^{25}$: 1.5573. Analysis: Observed: C 78.10; H 11.85; N 9.83; Theoretical: C 77.69; H 12.23; N 10.07.

EXAMPLE 8

Production of a polyurethane urea 200 g (0.1 mol) of hexane diol polycarbonate (MW 2000) are reacted at 100° C. with 49 g (0.22 mol) of 3-isocyanatomethyl-3,5,5-trimethyl cyclohexyl isocyanate until the expected isocyanate content is reached (after about 2 hours). The prepolymer melt is diluted with toluene and subsequently reacted at room temperature with 30 g (0.12 mol) of 9,10-diamino-1,4:5,8-dimethanotetradecahydroanthracene (amine IX of Example 1), dissolved in an inert solvent such as methylethyl ketone. The total quantity of solvent is calculated in such a way that a final concentration of 30% by weight of polyurethane urea is obtained. During the reaction of the prepolymer with the amine, the viscosity of the mixture rises to a final value of 30 to 40,000 cP/25° C. An almost colorless, clear solution is formed, giving a clear highly elastic light-stable and hydrolysis-stable film with the properties specified in the following Table on a variety of different substrates.

| | |
|---|---|
| Elongation at break (DIN 53504) | 460% |
| Tensile strength (DIN 53504) | 407 kp/cm² |
| Modulus at 100% elongation (DIN 53504) | 51 kp/cm² |
| Modulus at 200% elongation (DIN 53504) | 97 kp/cm² |
| Modulus at 300% elongation (DIN 53504) | 179 kp/cm² |
| Tensile strength and elongation at break after 400 hours Xeno testing | 387 kp/cm² 390% |
| Tensile strength and elongation at break after hydrolysis testing at 70° C/95% relative humidity | |
| After 7 days | 400 kp/cm²; 450% |
| After 14 days | 397 kp/cm²; 460% |
| After 56 days | 320 kp/cm²; 470% |
| Micro hardness Shore A (DIN 53505) | |
| Before | 66 |
| After storage for 21 days | 84 |
| Increase in volume (swelling) after storage for 2 hours in solvents: | |
| Trichlorethylene | 630% |
| Perchlorethylene | 82% |

The product has an extremely high resistance to hydrolysis, in comparison with polyurethane ureas obtained with conventional amines.

EXAMPLE 9

N,N'-Diisopropyl-9,10-diamino-1,4:5,8-dimethano-tetradecahydroanthracene (XVI)

Stage A Production of ketimine 123 g (0.5 mol) of 9,10-diamino-1,4:5,8-dimethano-tetradecahydroanthracene (IX) are heated on a water separator with 100 g of acetone, 300 ml of toluene and 0.3 g of p-toluene sulphonic acid until 18 ml of water have been removed from the circuit. The ketimine is then isolated by distilling off the solvent and is subsequently hydrogenated without further purification.

Stage B Hydrogenation 163 g (0.5 mol) of the ketimine produced in stage A are hydrogenated for 10 minutes at 120° to 130° C. under a hydrogen pressure of 150 bars in 600 ml of acetone in the presence of 200 g of platinized carbon (0.5% by weight Pt). After the catalyst has been separated off and the solvent distilled off, the N,N'-diisopropyl-9,10-diamino-1,4:5,8-dimethano-tetradecahydroanthracene (XIV) is obtained in a yield of 142 g (86%, based on the diketone III used) by distillation in a high vacuum at 138°–141° C./0.13 Torr.

$n_D^{25}$: 1.5168. Analysis: Observed: C 79.9; H 11.4; N 8.6; Theoretical: C 80.0; H 11.5; N 8.48.

What is claimed is:

1. Compounds corresponding to the general formula

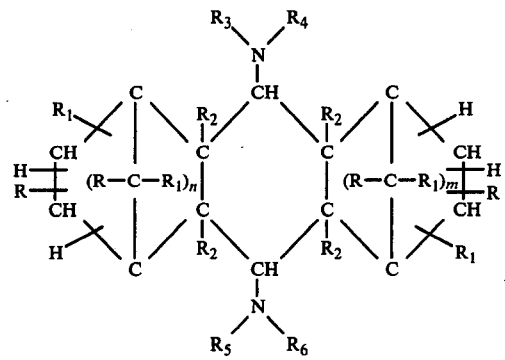

in which
n and m which are the same or different have the values 1 or 2,
R, $R_1$, and $R_2$ which are the same or different, represent hydrogen or —$CH_3$ groups, and
$R_3$ and $R_5$ represent hydrogen, and
$R_4$ and $R_6$ represent hydrogen, a $C_1$–$C_{18}$ alkyl group, or a cycloalkyl group with 5 to 8 carbon atoms.

2. The compounds of claim 1 wherein $R_4$ and $R_6$ represent a $C_1$–$C_4$ alkyl group which may be branched and/or contain a hydroxyl group and/or an ether group.

3. The compounds of claim 1, in which $R_3$, $R_4$, $R_5$ and $R_6$ represent hydrogen.

4. The compounds of claim 1, in which $R_2$, $R_3$, $R_4$, $R_5$ and $R_6$ represent hydrogen.

* * * * *